United States Patent
Zou

(10) Patent No.: US 8,648,180 B2
(45) Date of Patent: Feb. 11, 2014

(54) COMPOUND SMILAXCHINOSIDE F

(75) Inventor: Jieming Zou, Guilin (CN)

(73) Assignee: Guilin Sanjin Pharmaceuticals Co., Ltd., Guilin, Guangxi Zhang Autonomous Region (CN)

( * ) Notice: Subject to any disclaimer, the term of this patent is extended or adjusted under 35 U.S.C. 154(b) by 0 days.

(21) Appl. No.: 13/702,464

(22) PCT Filed: Jun. 24, 2010

(86) PCT No.: PCT/CN2010/074375
§ 371 (c)(1),
(2), (4) Date: Dec. 6, 2012

(87) PCT Pub. No.: WO2011/153719
PCT Pub. Date: Dec. 15, 2011

(65) Prior Publication Data
US 2013/0090461 A1 Apr. 11, 2013

(30) Foreign Application Priority Data
Jun. 8, 2010 (CN) .......................... 2010 1 0194619

(51) Int. Cl.
*C07J 41/00* (2006.01)
*C07J 17/00* (2006.01)
*C07G 3/00* (2006.01)

(52) U.S. Cl.
USPC ...................... 536/5; 536/6; 536/6.1; 536/6.3

(58) Field of Classification Search
None
See application file for complete search history.

(56) References Cited

FOREIGN PATENT DOCUMENTS

| CN | 1727358 A | 2/2006 |
| CN | 1763077 A | 4/2006 |
| CN | 101011545 A | 8/2007 |

OTHER PUBLICATIONS

International Search Report (PCT/ISA/210) issued on Mar. 10, 2011, by the Chinese Patent Office as the International Searching Authority for International Application No. PCT/CN2010/074375.

*Primary Examiner* — Traviss C McIntosh, III
(74) *Attorney, Agent, or Firm* — Buchanan Ingersoll & Rooney PC

(57) ABSTRACT

Smilaxchinoside F compound and its separation method are disclosed. The compound has the structure as following. The use of Smilaxchinoside F in the manufacture of a medicine for treating abnormal angiogenesis and its relating diseases is also disclosed.

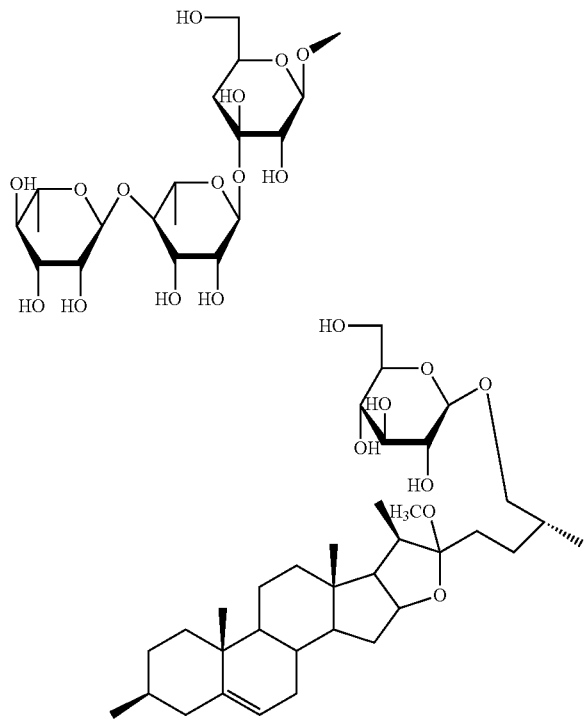

9 Claims, 11 Drawing Sheets

COMPOUND SMILAXCHINOSIDE F

FIELD OF THE INVENTION

The present invention relates to a new compound and its separation method. More specifically, it relates to a new compound called Smilaxchinoside F and its separation method.

BACKGROUND OF THE INVENTION

Smilax is the dry rhizome of a liaceae plant, Smilax china L, which is also called Jingangteng. As a traditional Chinese herb, Smilax was collected into Chinese Pharmacopoeia 2005 version due to its efficacy in expelling evil-wind, removing dampness, detoxification and eliminating blood stasis. It is used for soreness and pain of tendon and bones, excessive urine, excessive leucorrhea, and swelling of hard furuncle. In Chinese clinical practice, it is used not only for treatment of gynecological diseases but also for cancer treatment and shows good curative effect.

Much research has been done about the chemical components of Smilax plants. So far more than 80 compounds have been separated from them, including flavones, steroidal saponins, stilbene glucosides, amino acids, tannins, etc. Among these compounds, flavones and steroidal saponins are substances that have obvious anti-inflammation pharmacological activity.

Smilax plants generally contain flavone compounds. Currently more than 20 flavone compounds have been separated and identified from these plants. The basic core structure of these flavone compounds are flavonoids and flavonols, dihydroflavones and Dihydroflavonols, chalcones, and catechins.

Up till now, more than 30 steroidal saponins have been separated from Smilax plants. These steroidal saponins, based on their different structures of diosgenin, are divided into three categories, namely spirostanols, isospirostanols, and furostanols, among which spirostanols are dominant. The major four saccharides in saponins include: D-glucose, D-galactose, L-rhamnose, and L-arabinose, which form a variety of saponins with sapogenin in different ways.

In this invention, a systematic separation and purification study is performed using multiple chromatography techniques over the extracts of the Smilax china L. rhizome by 70% acetone or ethanol or methanol. In addition, the structures of the compounds obtained by extraction and separation are identified using modern spectral techniques. A new compound, named Smilaxchinoside F, is obtained by separation. Hence, this invention is fulfilled.

SUMMARY OF THE INVENTION

The first object of the present invention is to provide a new compound, Smilaxchinoside F, which is extracted from the liaceae plant Smilax china L.

The second object of the present invention is to provide an extraction and separation method for the said new compound Smilaxchinoside F.

The third object of the present invention is to provide the applications of the said new compound Smilaxchinoside F.

In order to achieve the first object of the present invention, the following technical solution is used:

The new compound Smilaxchinoside F has the following structure,

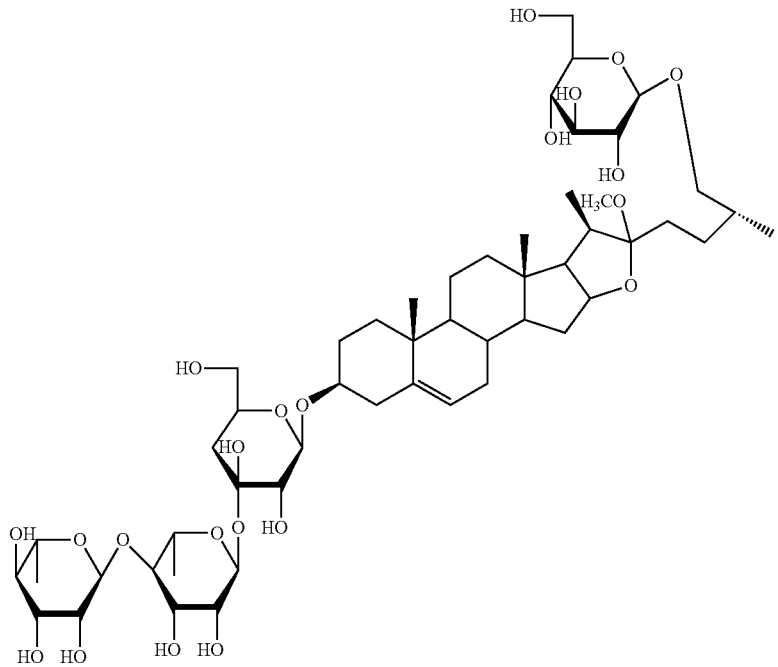

In order to achieve the second object of the present invention, the following technical solution is used:

The method for separating Smilaxchinoside F comprising the following steps,

2) Extraction and Coarse Separation

The crude powder of Smilax china roots is extracted by organic solvents; the extraction liquid are combined; and then the organic solvents are recovered; a proper amount of water is added to form suspension liquid; the suspension liquid is extracted for 4~5 times with ethyl acetate and n-butanol sequentially; the solvents are recovered separately; and then ethyl acetate extracts and n-butanol extracts are obtained;

2) Separation of n-butanol Extracts the n-butanol extracts are adsorbed by DM130 macroporous resins, eluted with water, 25%, 50% and 75% of ethanol, respectively;

50% elution fraction of the n-butanol extracts are adsorbed by MCI gel filtration chromatography and 100~300 mesh silica gel column chromatography, eluted with 9:1:0.1~7:3:0.5 chloroform-methanol-H$_2$O;

a total of 31 fractions are collected; the fraction 7 to 9 are purified by Sephadex LH-20 gel filtration chromatography and are crystallized repeatedly to obtain Smilaxchinoside F compound.

Said *Smilax china* roots is dry and the fresh in present invention. The flowchart for the extraction and separation of *smilax* is shown in FIG. 1. The flowchart for the separation of n-butanol fraction is shown in FIG. 2.

The obtained compounds vary with different column packing materials. The compound of the present invention is obtained by using specific chromatography for different fractions after a large number of experiments.

In the method for separating Smilaxchinoside F provided by the present invention, the organic solvent in step 1 is 70% of acetone or ethanol or methanol.

In the method for separating Smilaxchinoside F provided by the present invention, the organic solvent in step 1 is 70% acetone.

In the method for separating Smilaxchinoside F provided by the present invention, the extraction in step 1 is impregnation extraction, reflux extraction or ultrasonic extraction.

In the method for separating Smilaxchinoside F provided by the present invention, said impregnation extraction in step 1 is, impregnation extraction at room temperature for 3-5 times, particularly 4 times; and 20~30 hours each time, particularly 24 hours.

In the method for separating Smilaxchinoside F provided in the present invention, the reflux extraction in step 1 is reflux extraction for 1~3 times, 1~3 hours each time.

In the method for separating Smilaxchinoside F provided in the present invention, the ultrasonic extraction in step 1 is ultrasonic extraction for 1~3 times, 1~3 hours each time.

The third object of the present invention is to provide application of Smilaxchinoside F, specifically, to provide the application of said Smilaxchinoside F for manufacturing a medicament for the treatment of diabetic retinopathy, atherosclerosis, rheumatoid arthritis, systemic sclerosis, and tumor diseases; more specifically, to provide the application of said Smilaxchinoside F for manufacturing a medicament for the treatment of diabetic retinopathy, atherosclerosis, rheumatoid arthritis, systemic sclerosis, and tumor diseases caused by vascular endothelial cell proliferation.

The invention demonstrates through experiments that not only does the new compound Smilaxchinoside F provided by present invention have an obvious inhibition effect on SPA cells, but also it has a significant inhibition effect on ECV-304. Furthermore, this inhibition effect shows obvious dose-effect and time-effect relationships, indicating an extensive application prospect of Smilaxchinoside F in the treatment of diseases related to angiogenesis.

The application of the new compound Smilaxchinoside F provided by present invention for the treatment of angiogenesis-related diseases means, specifically, its applications in the production of medicines that are used for treatment of diabetic retinopathy, atherosclerosis, rheumatoid arthritis, systemic sclerosis or tumor diseases. Especially it means the application of this compound for medicines that are used to treat diabetic retinopathy, atherosclerosis, rheumatoid arthritis, systemic sclerosis or tumor diseases that are caused by vascular endothelial cell proliferation.

DETAILED DESCRIPTION OF THE INVENTION

Figure 1:
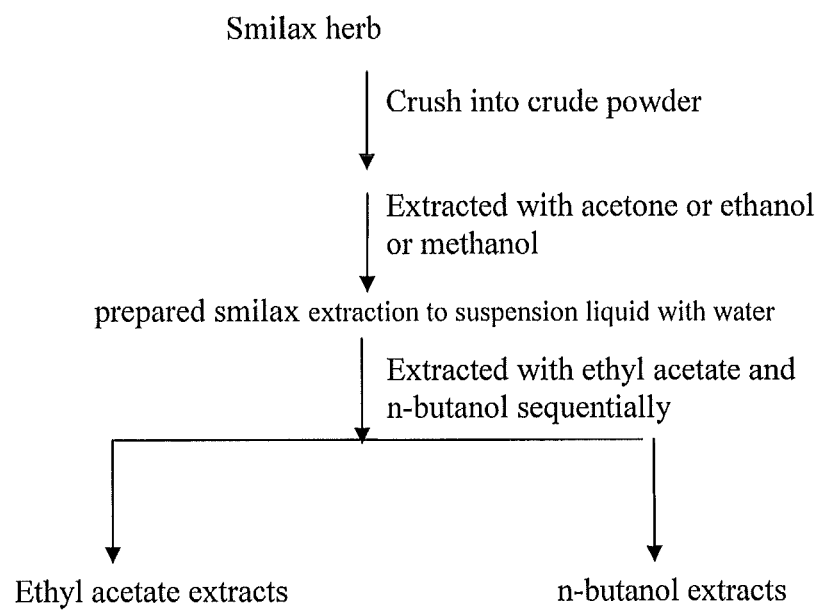
FIG. 1 Flowchart of extraction and separation of *Smilax*
FIG. 2 Flowchart of separation of n-butanol fraction
FIG. 3-1 Chemical structure of Smilaxchinoside F
FIG. 3-2 Stereo-configuration of Smilaxchinoside F
FIG. 4 $^{13}$H-NMR spectrum of Smilaxchinoside F
FIG. 5 $^{13}$C-NMR spectrum of Smilaxchinoside F
FIG. 6 HSQC spectrum of Smilaxchinoside F
FIG. 7 HMBC spectrum of Smilaxchinoside F
FIG. 8 HSQC-tocsy spectrum of Smilaxchinoside F
FIG. 9 ROESY spectrum of Smilaxchinoside F
FIG. 10 HR-ESI-MS spectrum of Smilaxchinoside F

The following are the examples of the present invention, the examples are used to better describe rather than limit the present invention.

Example 1

1) Extraction and Coarse Separation

The crude powder of *Smilax china* roots, 7 kg, is impregnation extraction with 70% acetone under room temperature for 4 times, 24 hours each time. The extraction liquid are combined and the acetone is recovered. A proper amount of water is added to the extract to form suspension liquid; the suspension liquid is extracted 4 times with ethyl acetate and n-butanol sequentially; the solvents are recovered separately; the ethyl acetate extracts and n-butanol extracts are obtained.

2) Separation of the n-butanol Extracts

The n-butanol extracts obtained in step 1) are adsorbed by DM130 macroporous resins and eluted in gradient using water, 25%, 50% and 75% of ethanol, respectively.

50% elution fraction of the n-butanol extracts, 100 g, are adsorbed by MCI gel filtration chromatography and 100 mesh silica gel column chromatography, eluted with 9:1:0.1~7:3:0.5 chlorform-methanol-H$_2$O. A total of 31 fractions are collected. The fraction 7 to 9 are purified by Sephadex LH-20 gel filtration chromatography and are crystallized repeatedly to obtain Smilaxchinoside F compound.

Example 2

1) Extraction and Coarse Separation

The crude powder of *Smilax china* roots, 7 kg, is impregnation extraction with 70% ethanol under room temperature for 4 times, 24 hours each time. The extraction liquid are combined and the ethanol is recovered. A proper amount of water is added to the extract to form suspension liquid; the suspension liquid is extracted 4 times with ethyl acetate and n-butanol sequentially; the solvents are recovered separately, and ethyl acetate extracts and n-butanol extracts are obtained.

2) Separation of the n-butanol Extracts

The n-butanol extracts obtained in step 1) are adsorbed by DM130 macroporous resins and eluted in gradient using water, 25%, 50% and 75% of ethanol, respectively.

50% elution fraction of the n-butanol extracts, 100 g, are adsorbed by MCI gel filtration chromatography and 300 mesh silica gel column chromatography, eluted with 9:1:0.1~7:3:0.5 chlorform-methanol-H$_2$O. A total of 31 fractions are collected. The fraction 7 to 9 are purified by Sephadex LH-20 gel filtration chromatography and are crystallized repeatedly to obtain Smilaxchinoside F compound.

Example 3

1) Extraction and Coarse Separation

The crude powder of *Smilax china* roots, 7 kg, is impregnation extraction with 70% methanol under room temperature for 4 times, 24 hours each time. The extraction liquid are combined and the methanol is recovered. A proper amount of water is added to the extract to form suspension liquid; the suspension liquid is extracted 4 times with ethyl acetate and n-butanol sequentially; the solvents are recovered separately, and ethyl acetate extracts and n-butanol extracts are obtained.

2) Separation of the n-butanol Extracts

The n-butanol extracts obtained in step 1) are adsorbed by DM130 macroporous resins and eluted in gradient using water, 25%, 50% and 75% of ethanol, respectively.

50% elution fraction of the n-butanol extracts, 100 g, are adsorbed by MCI gel filtration chromatography and 200 mesh silica gel column chromatography, eluted with 9:1:0.1~7:3:0.5 chlorform-methanol-H$_2$O. A total of 31 fractions are collected. The fraction 7 to 9 are purified by Sephadex LH-20 gel filtration chromatography and are crystallized repeatedly to obtain Smilaxchinoside F compound.

Example 4

1) Extraction and Coarse Separation

The crude powder of *Smilax china* roots, 7 kg, is reflux-extracted with 70% acetone for 3 times, 2 hours each time. The extraction liquid are combined and the acetone is recovered. A proper amount of water is added to the extract to form suspension liquid; the suspension liquid is extracted 5 times with ethyl acetate and n-butanol sequentially; the solvents are recovered separately, and ethyl acetate extracts and n-butanol extracts are obtained.

2) Separation of the n-butanol Extracts

The n-butanol extracts obtained in step 1) are adsorbed by DM130 macroporous resins and eluted in gradient using water, 25%, 50% and 75% of ethanol, respectively.

50% elution fraction of the n-butanol extracts, 100 g, are adsorbed by MCI gel filtration chromatography and 200 mesh silica gel column chromatography, eluted with 9:1:0.1~7:3:0.5 chlorform-methanol-H$_2$O. A total of 31 fractions are collected. The fraction 7 to 9 are purified by Sephadex LH-20 gel filtration chromatography and are crystallized repeatedly to obtain Smilaxchinoside F compound.

Example 5

1) Extraction and Coarse Separation

The crude powder of *Smilax china* roots, 7 kg, is reflux-extracted with 70% ethanol for 3 times, 2 hours each time. The extraction liquid are combined and the ethanol is recovered. A proper amount of water is added to the extract to form suspension liquid; the suspension liquid is extracted 4 times with ethyl acetate and n-butanol sequentially; the solvents are recovered separately, and ethyl acetate extracts and n-butanol extracts are obtained.

2) Separation of the n-butanol Extracts

The n-butanol extracts obtained in step 1) are adsorbed by DM130 macroporous resins and eluted in gradient using water, 25%, 50% and 75% of ethanol, respectively.

50% elution fraction of the n-butanol extracts, 100 g, are adsorbed by MCI gel filtration chromatography and 200 mesh silica gel column chromatography, eluted with 9:1:0.1~7:3:0.5 chlorform-methanol-H$_2$O. A total of 31 fractions are collected. The fraction 7 to 9 are purified by Sephadex LH-20 gel filtration chromatography and are crystallized repeatedly to obtain Smilaxchinoside F compound.

Example 6

1) Extraction and Coarse Separation

Seven kilograms of the crude powder of *Smilax china* roots is reflux-extracted with 70% methanol for 3 times, 2 hours each time. The extraction liquid are combined and the methanol is recovered. A proper amount of water is added to the extract to form suspension liquid; the suspension liquid is extracted 4 times with ethyl acetate and n-butanol sequentially; the solvents are recovered separately, and so the ethyl acetate extracts and n-butanol extracts are obtained.

2) Separation of the n-butanol Extracts

The n-butanol extracts obtained in step 1) are adsorbed by DM130 macroporous resins and eluted in gradient using water, 25%, 50% and 75% of ethanol, respectively.

A hundred grams of 50% elution fraction of the n-butanol extracts are adsorbed by MCI gel filtration chromatography and 200 mesh silica gel column chromatography, eluted with 9:1:0.1~7:3:0.5 chlorform-methanol-H$_2$O. A total of 31 fractions are collected. The fraction 7 to 9 are purified by Sephadex LH-20 gel filtration chromatography and are crystallized repeatedly to obtain Smilaxchinoside F compound.

Example 7

1) Extraction and Coarse Separation

Seven kilograms of the crude powder of *Smilax china* roots is treated using ultrasonic extraction with 70% acetone for 3 times, 1 hour each time. The extraction liquid are combined and the acetone is recovered. A proper amount of water is added to the extract to form suspension liquid; the suspension liquid is extracted 4 times with ethyl acetate and n-butanol sequentially; the solvents are recovered separately, and so the ethyl acetate extracts and n-butanol extracts are obtained.

2) Separation of the n-butanol Extracts

The n-butanol extracts obtained in step 1) is are adsorbed by DM130 macroporous resins and eluted in gradient using water, 25%, 50% and 75% of ethanol, respectively.

50% elution fraction of the n-butanol extracts, 100 g, are adsorbed by MCI gel filtration chromatography and 200 mesh silica gel column chromatography, eluted with 9:1:0.1~7:3:0.5 chlorform-methanol-H$_2$O. A total of 31 fractions are collected. The fraction 7 to 9 are purified by Sephadex LH-20 gel filtration chromatography and are crystallized repeatedly to obtain Smilaxchinoside F compound.

Example 8

1) Extraction and Coarse Separation

Seven kilograms of the crude powder of *Smilax china* roots is treated using ultrasonic extraction with 70% ethanol for 3 times, 1 hour each time. The extraction liquid are combined and the ethanol is recovered. A proper amount of water is added to the extract to form suspension liquid; the suspension liquid is extracted 4 times with ethyl acetate and n-butanol sequentially; the solvents are recovered separately, and so the ethyl acetate extracts and n-butanol extracts are obtained.

2) Separation of the n-butanol Extracts

The n-butanol extracts obtained in step 1) is are adsorbed by DM130 macroporous resins and eluted in gradient using water, 25%, 50% and 75% of ethanol, respectively.

50% elution fraction of the n-butanol extracts, 100 g, are adsorbed by MCI gel filtration chromatography and 200 mesh silica gel column chromatography, eluted with 9:1:0.1~7:3:0.5 chlorform-methanol-$H_2O$. A total of 31 fractions are collected. The fraction 7 to 9 are purified by Sephadex LH-20 gel filtration chromatography and are crystallized repeatedly to obtain Smilaxchinoside F compound.

Example 9

1) Extraction and Coarse Separation

Seven kilograms of dry crude powder of *Smilax china* roots is treated using ultrasonic extraction with 70% methanol for 3 times, 1 hour each time. The extraction liquid are combined and the methanol is recovered. A proper amount of water is added to the extract to form suspension liquid; the suspension liquid is extracted 4 times with ethyl acetate and n-butanol sequentially; the solvents are recovered separately, and so the ethyl acetate extracts and n-butanol extracts are obtained.

2) Separation of the n-butanol Extracts

The n-butanol extracts obtained in step 1) are adsorbed by DM130 macroporous resins and eluted in gradient using water, 25%, 50% and 75% of ethanol, respectively.

50% elution fraction of the n-butanol extracts, 100 g, are adsorbed by MCI gel filtration chromatography and 200 mesh silica gel column chromatography, eluted with 9:1:0.1~7:3:0.5 chlorform-methanol-$H_2O$. A total of 31 fractions are collected. The fraction 7 to 9 are purified by Sephadex LH-20 gel filtration chromatography and are crystallized repeatedly to obtain Smilaxchinoside F compound.

Example 10

1) Extraction and Coarse Separation

Seven kilograms of dry crude powder of *Smilax china* roots is impregnation extraction under room temperature with 70% ethanol for 5 times, 23 hours each time. The extraction liquid are combined and the ethanol is recovered. A proper amount of water is added to the extract to form suspension liquid; the suspension liquid is extracted 4 times with ethyl acetate and n-butanol sequentially; the solvents are recovered separately, and so the ethyl acetate extracts and n-butanol extracts are obtained.

2) Separation of the n-butanol Extracts

The n-butanol extracts obtained in step 1) is are adsorbed by DM130 macroporous resins and eluted in gradient using water, 25%, 50% and 75% of ethanol, respectively.

50% elution fraction of the n-butanol extracts, 100 g, are adsorbed by MCI gel filtration chromatography and 200 mesh silica gel column chromatography, eluted with 9:1:0.1~7:3:0.5 chlorform-methanol-$H_2O$. A total of 31 fractions are collected. The fraction 7 to 9 are purified by Sephadex LH-20 gel filtration chromatography and are crystallized repeatedly to obtain Smilaxchinoside F compound.

Example 11

1) Extraction and Coarse Separation

Seven kilograms of the crude powder of *Smilax china* roots is impregnation extraction with 70% acetone for 4 times, 24 hour each time. The extraction liquid are combined and the acetone is recovered. A proper amount of water is added to the extract to form suspension liquid; the suspension liquid is extracted 5 times with ethyl acetate and n-butanol sequentially; the solvents are recovered separately, and so 270 grams of ethyl acetate fraction extracts and 460 grams of n-butanol extracts are obtained 2) Separation of the n-butanol Extracts Four hundred and sixty grams of the n-butanol extracts obtained in step 1) are adsorbed by DM130 macroporous resins and eluted in gradient using water, 25%, 50% and 75% of ethanol, respectively.

A hundred grams of 50% elution fraction of the n-butanol extracts are adsorbed by MCI gel filtration chromatography and 200 mesh silica gel column chromatography, eluted with 9:1:0.1~7:3:0.5 chlorform-methanol-$H_2O$. A total of 31 fractions are collected. The fraction 7 to 9 are purified by Sephadex LH-20 gel filtration chromatography and are crystallized repeatedly to obtain Smilaxchinoside F compound.

Test Example 1

Structure Identification of the New Compound Smilaxchinoside F

This experiment is carried out to identify the structure of the new compound Smilaxchinoside F prepared according to the present invention.

The new compound Smilaxchinoside F prepared in example 1 of the present invention is white powder and solved by methanol easily. HR-ESI-MS spectra show that the molecular ion peak is at 1061.5525 [M+Na]$^+$ (namely $C_{52}H_{85}O_{22}$); the molecular formula is $C_{52}H_{86}O_{22}$; the degree of unsaturation is 10. $^1H$ NMR spectra show that there are two single-peak methyls, four double-peak methyls, one oxidized methine [$\delta3.62$ (1H, m, H-3)], one methoxy [$\delta3.25$ (3H, s, 22-OCH$_3$)], one alkene hydrogen [$\delta5.52$ (1H, br d, J=5.3 Hz, H-6)], and four sugar anomeric proton signals [$\delta4.85$ (1H, d, J=7.7 Hz, Glc-H-1''''), 4.97 (1H, d, J=7.2 Hz, Glc-H-1'), 5.87 (1H, br s, Rha-H-1''), 6.42 (1H, brs, Rha-H-1''')]. $^{13}C$ NMR also shows that there are six methyls, one methoxy, one oxidized methine, two trisubstituted double-bonds, and four sugar carbon signals. In addition, carbon spectra show that there are 27 carbon signals and by analysis of its degree of unsaturation and molecular formula, it was preliminarily deduced that it is a pentacyclic steroidal saponin compound.

26-diol-3-O-an α-L-rhamnose glycosyl-(1→4)-α-L-rhamnose glycosyl-(1→4)-O-β-D-glucopyranose. After Scifinder search, the compound is a new compound, named: Smilaxchinoside F.

Chemical structure 1-1

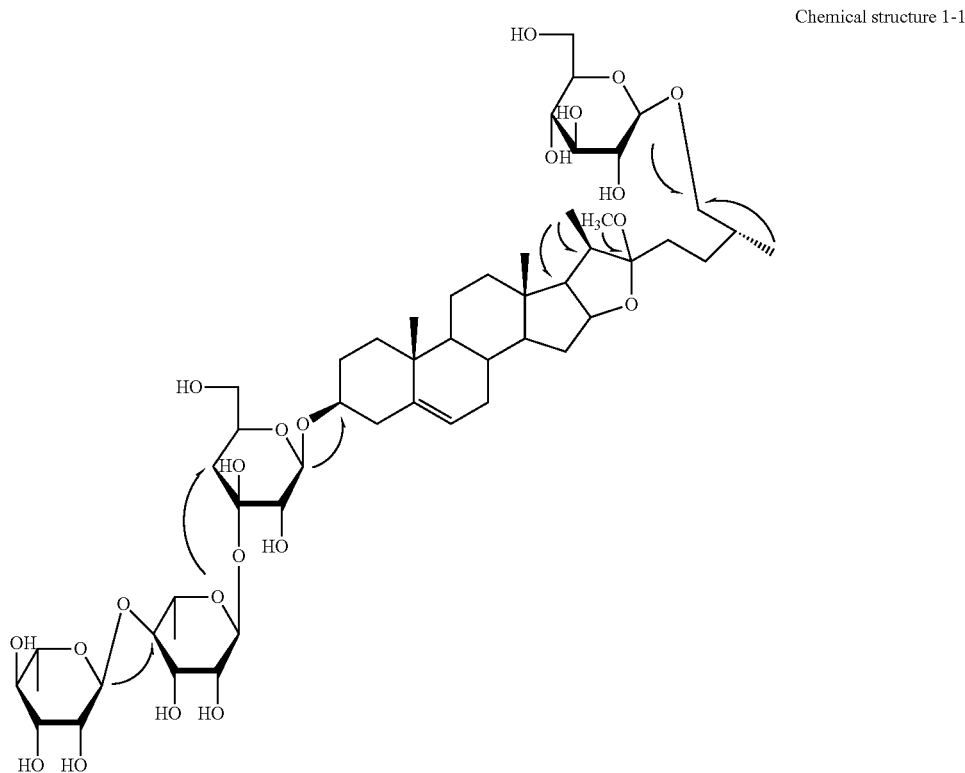

$^{13}$C NMR shows that the characteristic peak of furostan frame $C_{22}$ appears at [δ112.7 (s)]. Based on the literature (Bing Feng, Liping Kang, Baiping Ma, et al. The substrate specificity of a glucoamylase with steroidal saponin-rhamnosidase activity from curvularia lunata. *Tetrahedron*, 63 (2007), 6796-6812), the aglycone is deduced to be 22α-methoxy-(25R)-furostan-5-ene-3β,26-diol. Compared with the data of carbohydrate, they are terminal β-D-glucose, 4-substituted β-D-glucose, 4-substituted α-L-rhamnose, and terminal α-L-rhamnose in the compound.

HMBC spectra show that $^{13}$C—$^1$H between glucose H-1'''' and aglycone C-26, glucose H-1' and the aglycone C-3, rhamnose H-1'' and glucose C-4', and rhamnose H-1''' and rhamnose C-4'' are remotely related, which indicate the glucose C-1 is connected to sterane C-26. The other three carbohydrate connected successively by glucose C-1 and sterane C-3 positions (see structural formula 1-1). The connection order is consistent with carbohydrate connection order reported in reference (Bing Feng, Liping Kang, Baiping Ma, et al. The substrate specificity of a glucoamylase with steroidal saponin-rhamnosidase activity from curvularia lunata. *Tetrahedron*, 63 (2007), 6796-6812). The relevant data are shown in Table 1-1.

Figure 2:
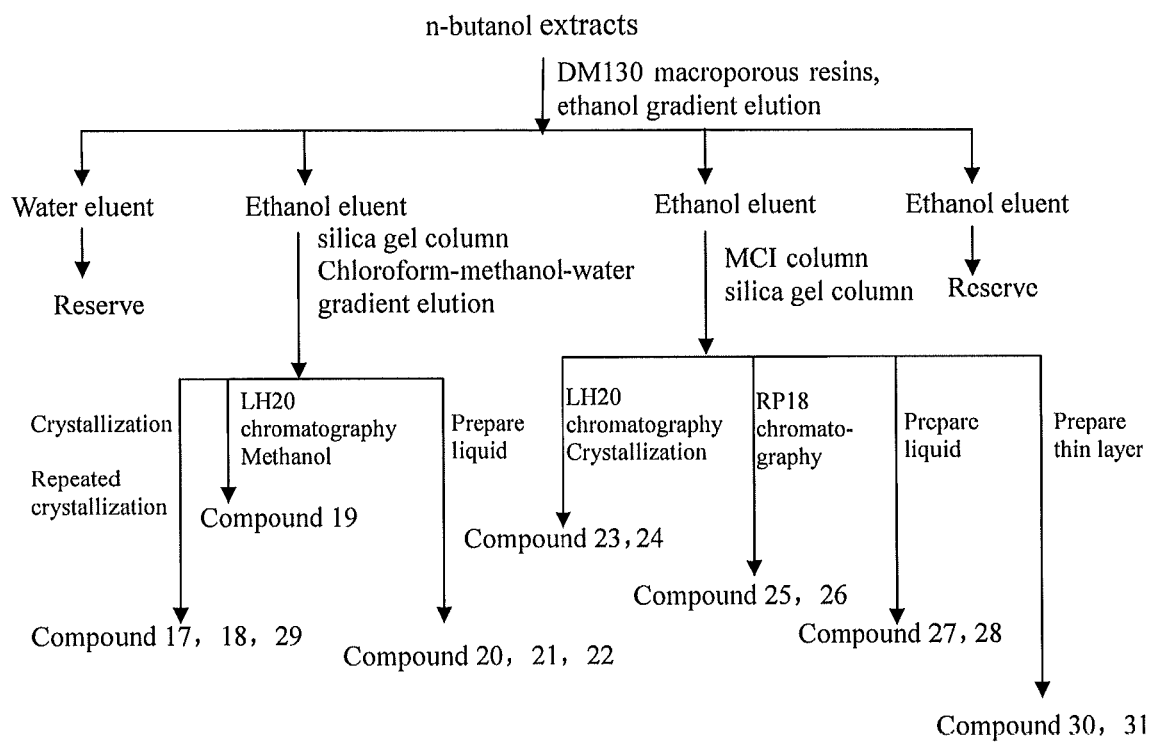
Figures 1, 3:
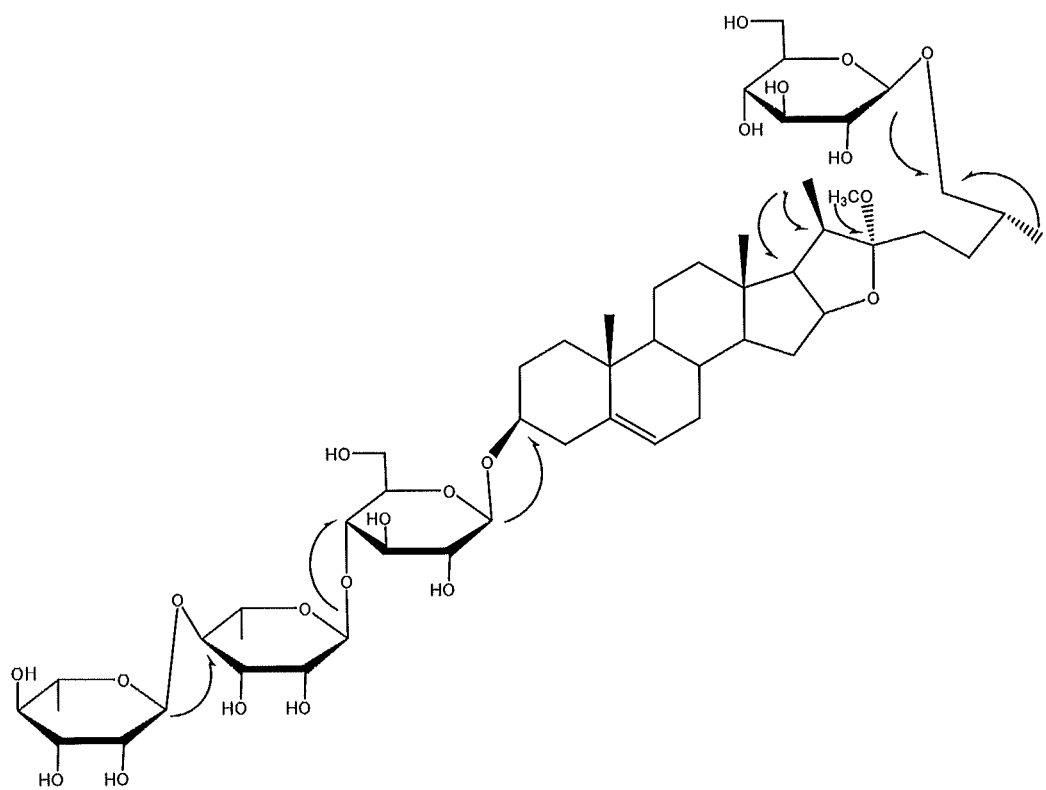
Figures 2, 3:
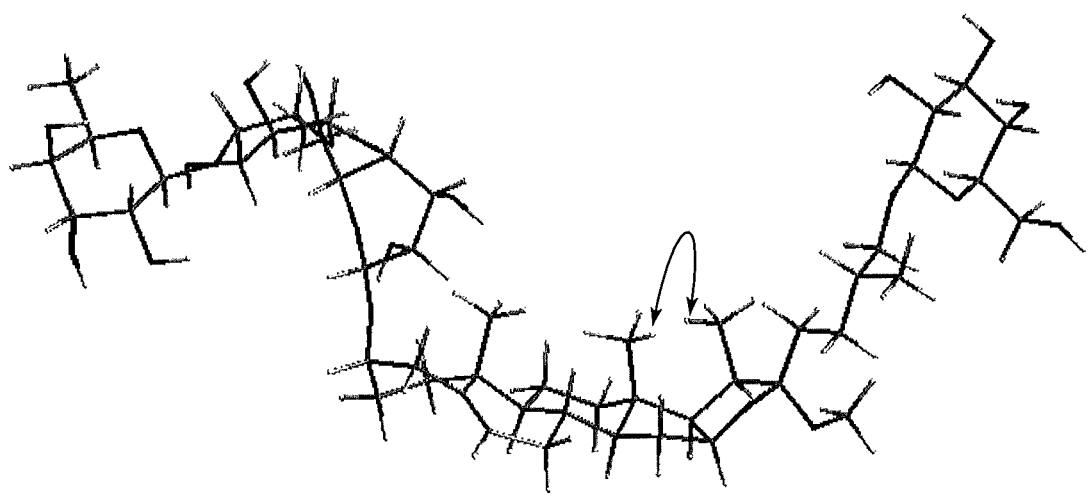
Figure 4:
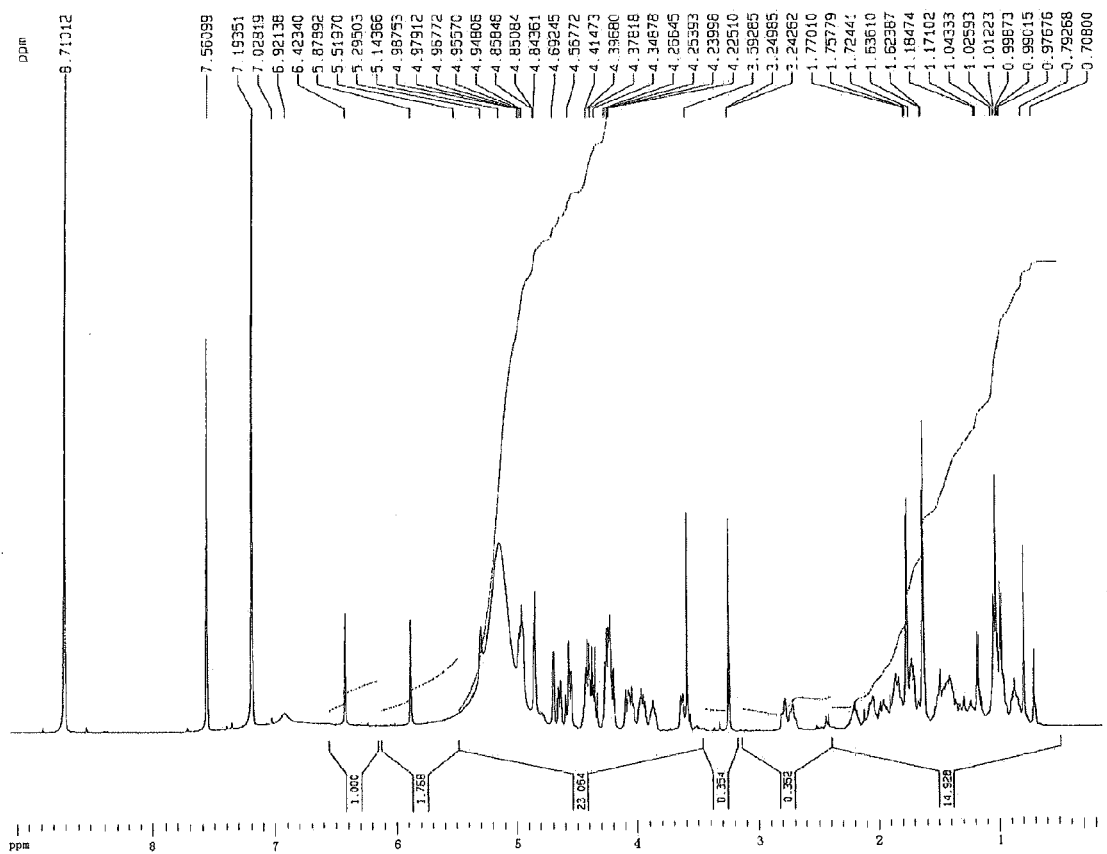
Figure 5:
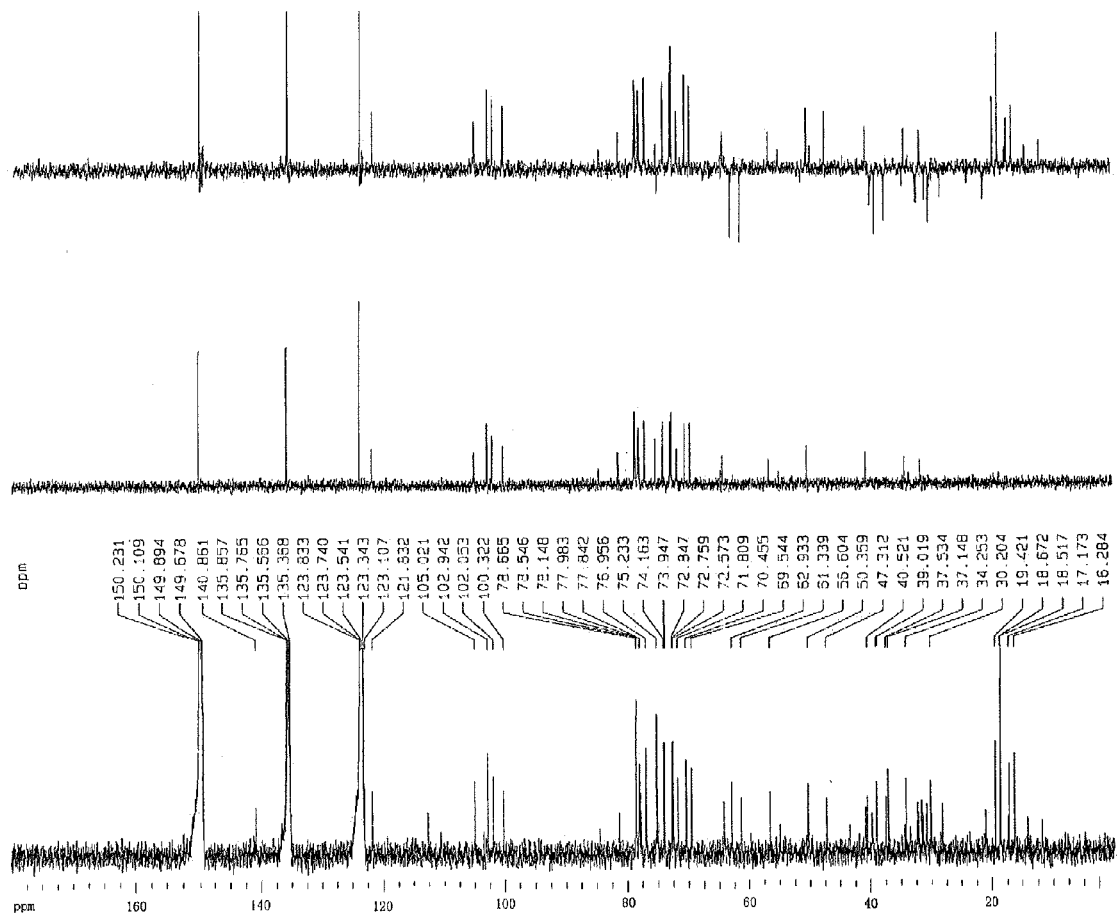
Figure 6:
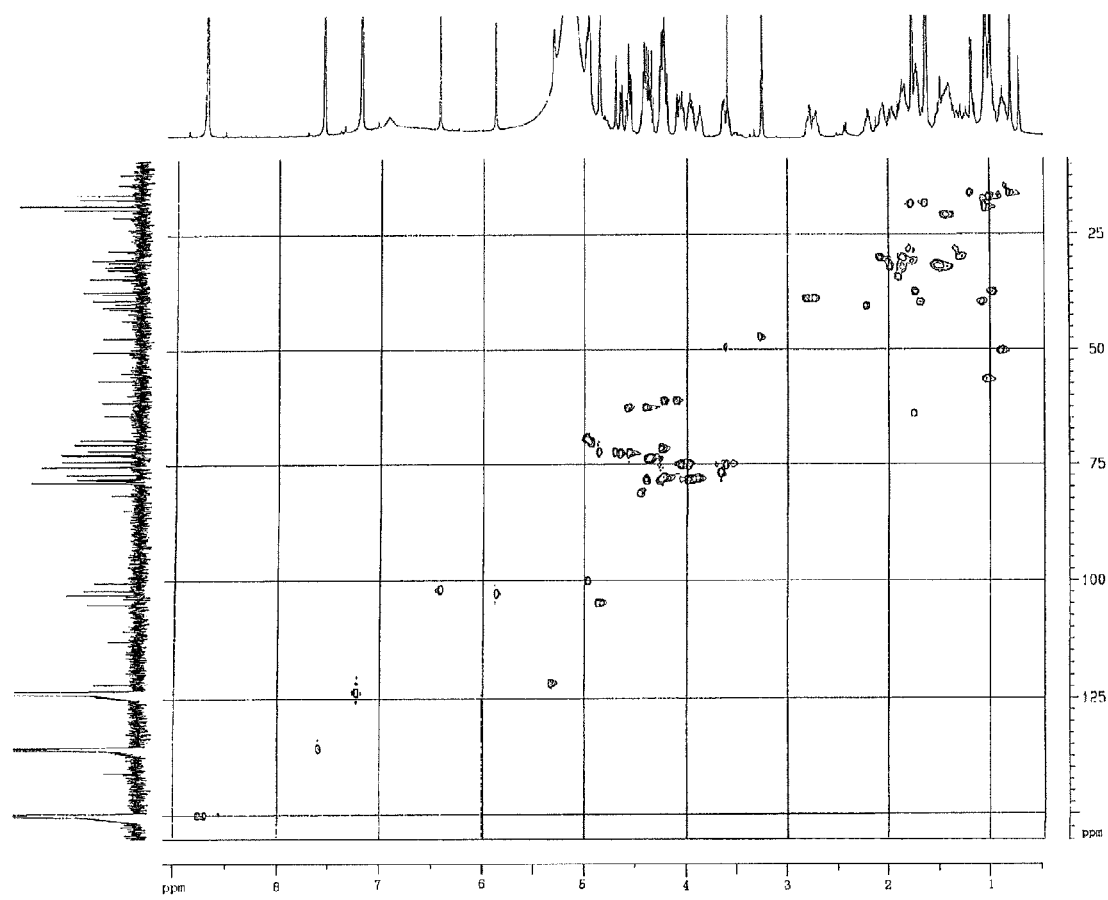
Figure 7:
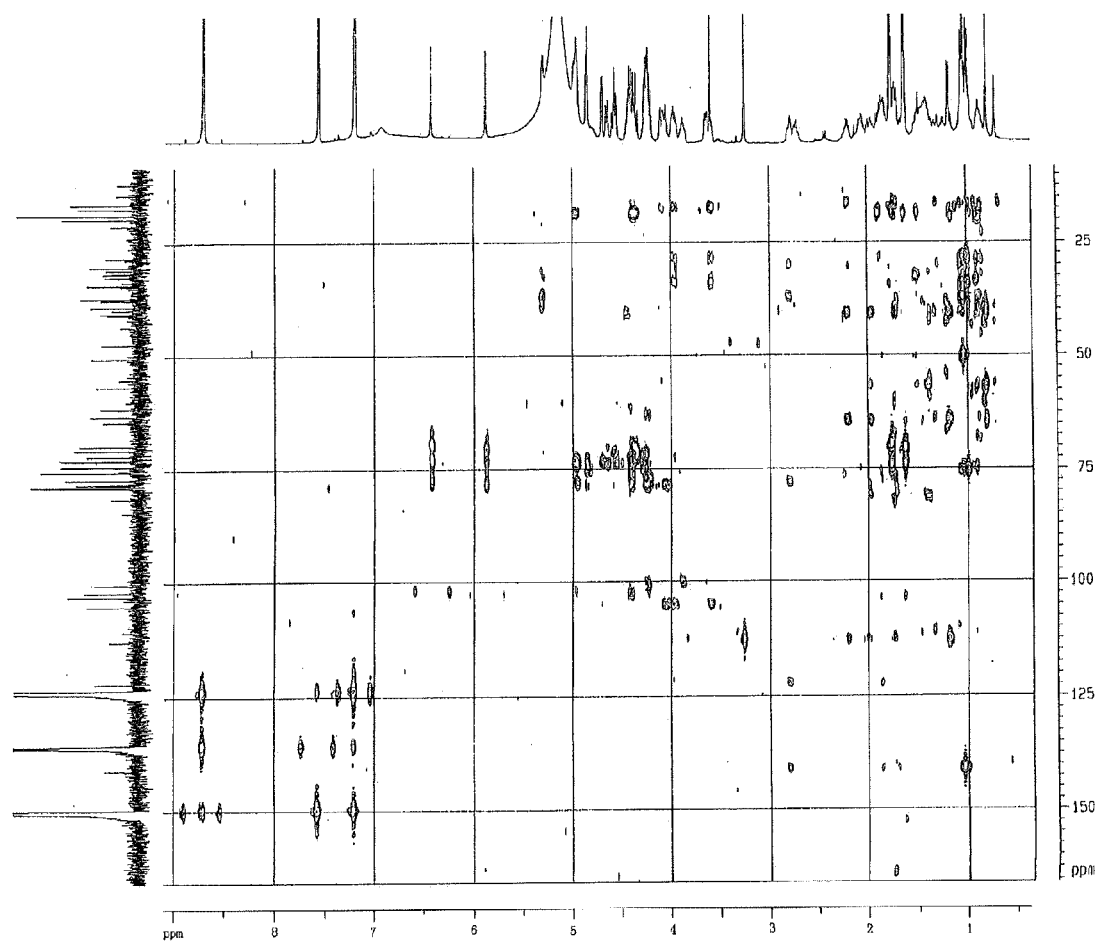
Figure 8:
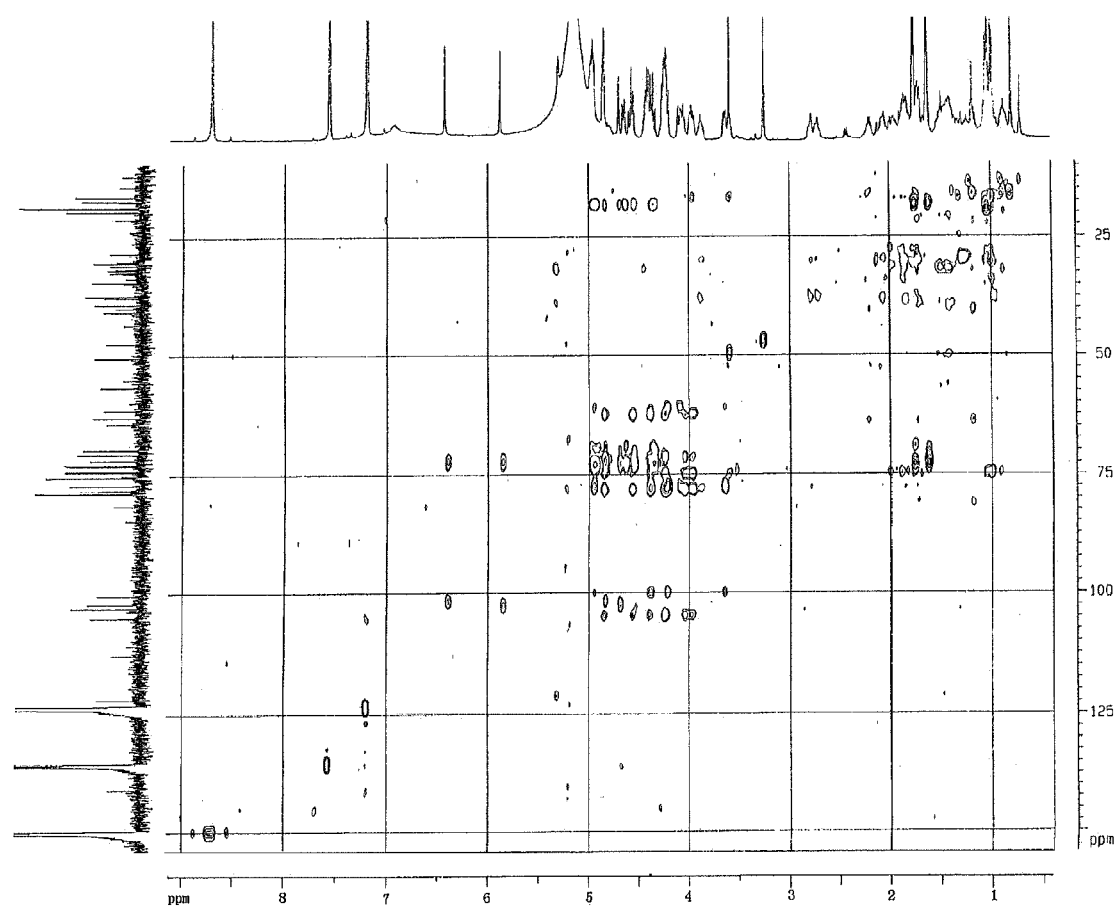
Figure 9:
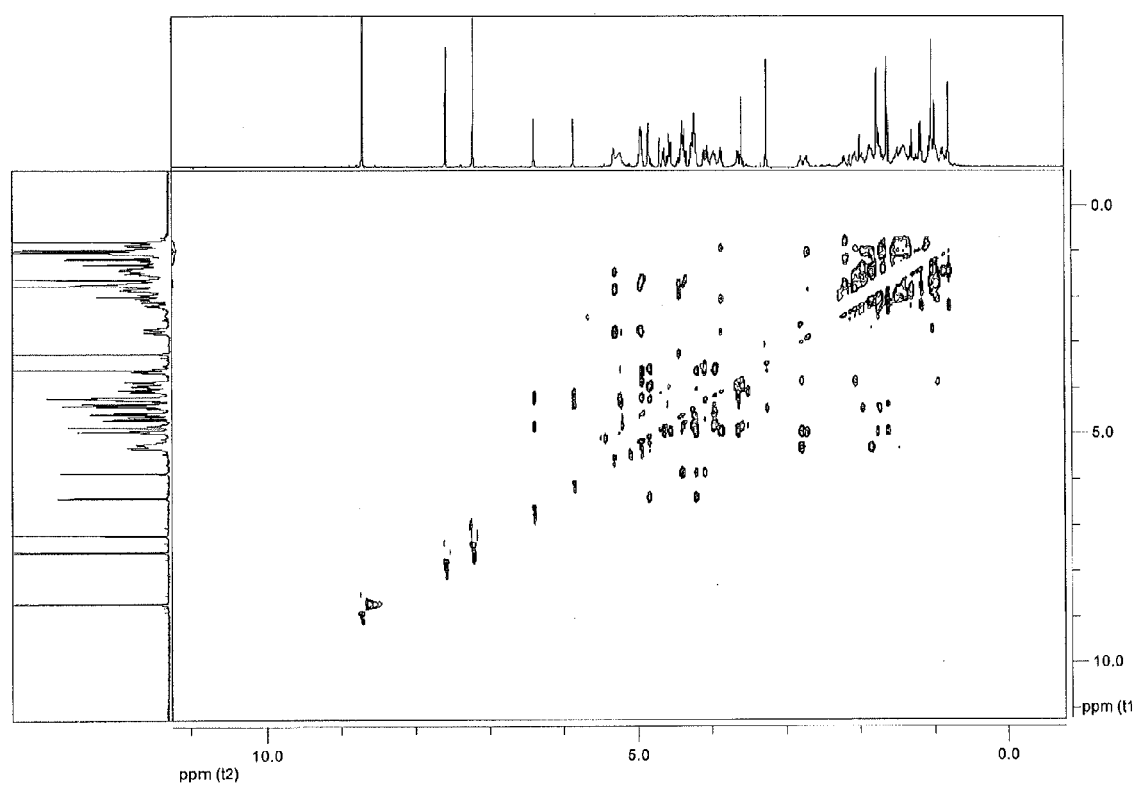
Figure 10:
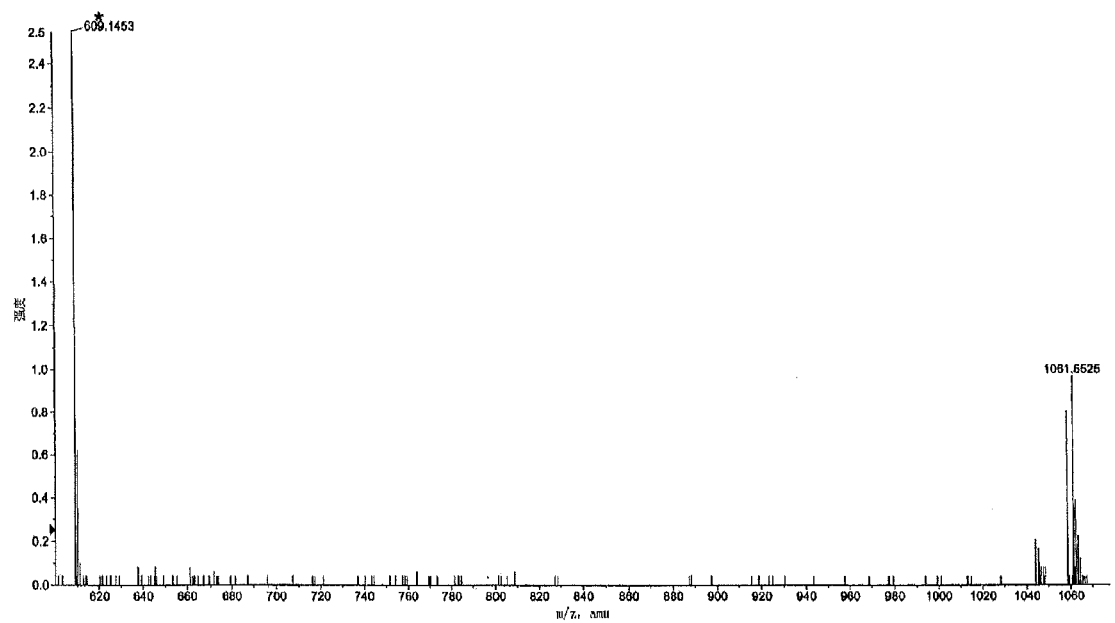

In addition, from ROSEY related spectra, it can be seen that the 18CH$_3$ and 21CH$_3$ are related, which confirmed that 21CH$_3$ is upward (see FIG. 3-2 the stereo-configuration of Smilaxchinoside F).

In summary, the structure of this compound is: 26-O-β-D-glucopyranosyl-22α-methoxy-(25R)-furostanol-5-ene-3β,

TABLE 1-1

$^1$H and $^{13}$C-NMR data of Smilaxchinoside F

| No | δ$_C$ | δ$_H$ (J=) | No | δ$_C$ | δ$_H$ (J=) |
|---|---|---|---|---|---|
| 1 | 37.5 t | | Glc I-1' | 100.3 d | 4.97 d (7.2) |
| 2 | 30.8 t | | 2' | 75.2 d | |
| 3 | 78.1 d | 3.62 m | 3' | 77.0 d | |
| 4 | 39.0 t | | 4' | 78.0 d | |
| 5 | 140.9 s | | 5' | 77.8 d | |
| 6 | 121.8 d | | 6' | 61.3 t | |
| 7 | 32.3 t | | Rha I-1'' | 102.9 d | 5.87 brd (5.3) |
| 8 | 32.1 d | | 2'' | 72.8 d | |
| 9 | 50.4 d | | 3'' | 73.9 d | |
| 10 | 37.1 s | | 4'' | 74.2 d | |
| 11 | 21.5 t | | 5'' | 69.5 d | |
| 12 | 40.2 t | | 6'' | 18.7 t | 1.76 d (6.0) |
| 13 | 40.8 s | | Rha II-1''' | 102.0 d | 6.42 brs |
| 14 | 56.6 d | | 2''' | 72.6 d | |
| 15 | 32.6 t | | 3''' | 72.8 d | |
| 16 | 81.6 d | | 4''' | 78.7 d | |
| 17 | 64.6 d | | 5''' | 70.4 d | |
| 18 | 16.2 q | 1.01 s | 6''' | 19.4 q | 1.63 d (6.2) |
| 19 | 18.5 q | | Glc I-1'''' | 105.0 d | 4.85 d (7.7) |
| 20 | 40.5 d | | 2'''' | 75.2 d | |
| 21 | 16.7 q | 1.71 d (7.0) | 3'''' | 78.7 d | |
| 22 | 112.7 s | | 4'''' | 71.8 d | |
| 23 | 31.7 t | | 5'''' | 78.5 d | |
| 24 | 28.2 t | | 6'''' | 62.9 t | |
| 25 | 34.2 d | | C$_{22}$—OMe | 47.6 q | 3.65 s |
| 26 | 75.7 t | | | | |
| 27 | 17.2 q | 0.99 d (7.0) | | | |

Structural identification is also performed for the Smilaxchinoside F prepared in other embodiments in present invention, and the same results are obtained.

Test Example 2

The Inhibition of Smilaxchinoside F on Lung Cancer Cell Line (SPC-A1)

I. Materials and Methods

1. Cell Lines:

Human lung cancer cells Spc-A1 (hereinafter referred to as SPC), is purchased from Wuhan Cell Collection Center (cell bank of China Center for Type CultureCollection).

2. Cell Culture and Experimental Groups

The tumor cells are placed in the RPMI-1640 complete medium including 10% fetal calf serum and are cultured at 37° C. under 5% $CO_2$ incubator. When the cell growth reaches the logarithmic phase (approximately 80% integration), cells are subcultured. The experiments are divided into negative control group (RPMI-1640), positive drug group (5Fu, $10^{-4}$ mol·$L^{-1}$) and reagent group of Smilaxchinoside F at different concentrations, which are prepared by Guilin Sanjin Pharmaceutical Co., Ltd, in accordance with example 1 of the present invention.

3. MTT Method $5\times10^7 \cdot L^{-1}$ cells at logarithmic phase are seeded in 96-well plates, each well 180 µL. After culturing for 24 h, medicine is added, each well 20 µL, five parallel wells for each group. On 4 hours before the end of culture, 20 µL of 5 g·$L^{-1}$ MTT solution is added to the each well. After the end of the culture (48 h and 72 h), the supernatant is discarded. 150 µL of DMSO is added to each wells; the optical density (A value) of each well is detected by a microplate reader at 490 nm; the tumor suppression percentage is calculated.

II. Results

The Impact of Smilaxchinoside F on Anti-SPA Proliferation In Vitro

The results show that 5Fu has significant anti-tumor effect, with the 48 and 72 hours inhibition percentage at 39.4% and 59.6%, respectively. Smilaxchinoside F has significant inhibitory effect on SPA cells, with the inhibition percentage of the 48 hour and the 72 hour at 46.5% and 53.5%, respectively. The IC50 of the 48 hour and the 72 hour are 113.5 µg/mL and 56.94 µg/mL, respectively, as shown in Table 1 and 2.

TABLE 1

The A values ($\bar{x} \pm s$, n = 5) of Smilaxchinoside F for anti-SPA cells proliferation in vitro (48 h)

| Groups | Dose | OD value | T-test | Inhibition rate (%) | IC50 |
|---|---|---|---|---|---|
| Negative control | — | 0.614 ± 0.058 | — | — | — |
| 5Fu (mol/L) | $10^{-4}$ | 0.372 ± 0.031 | 4E−05 | 39.37 | — |
| Szy1-20 (µg/ml) | 100 | 0.329 ± 0.01 | 5E−06 | 46.45 | 113.5 µg/ml |
| | 50 | 0.396 ± 0.053 | 3E−04 | 35.43 | |
| | 25 | 0.481 ± 0.065 | 0.009 | 21.68 | |
| | 12.5 | 0.506 ± 0.047 | 0.012 | 17.57 | |
| | 6.25 | 0.547 ± 0.029 | 0.052 | 10.82 | |
| | 3.125 | 0.570 ± 0.042 | 0.215 | 7.04 | |
| | 1.5625 | 0.582 ± 0.035 | 0.322 | 5.22 | |
| | 0.7813 | 0.603 ± 0.069 | 0.792 | 1.79 | |

TABLE 2

The A values ($\bar{x} \pm s$, n = 5) of Smilaxchinoside F for anti-SPA cells proliferation (72 h) in vitro

| Groups | Dose | OD value | T-test | Inhibition rate (%) | IC50 |
|---|---|---|---|---|---|
| Negative control | — | 0.731 ± 0.125 | — | — | — |
| 5Fu (mol/L) | $10^{-4}$ | 0.295 ± 0.026 | 6.086E−05 | 59.61 | — |
| Szy1-20 (µg/ml) | 100 | 0.340 ± 0.013 | 0.0001166 | 53.51 | 56.94 µg/ml |
| | 50 | 0.391 ± 0.032 | 0.0003593 | 46.60 | |
| | 25 | 0.419 ± 0.031 | 0.0006313 | 42.69 | |
| | 12.5 | 0.486 ± 0.077 | 0.0056688 | 33.61 | |
| | 6.25 | 0.549 ± 0.079 | 0.0244887 | 24.99 | |
| | 3.125 | 0.558 ± 0.032 | 0.0168241 | 23.76 | |
| | 1.5625 | 0.658 ± 0.078 | 0.2984153 | 10.04 | |
| | 0.7813 | 0.696 ± 0.024 | 0.5535656 | 4.81 | |

The same experiments are performed to Smilaxchinoside F prepared in other embodiments in the present invention, similar results are obtained.

Test Example 3

The Inhibitory Effect of Smilaxchinoside F on Vascular Endothelial Cell Line (ECV-304)

I. Materials and Method

Materials and Equipment

Vascular endothelial cell line (ECV-304): purchased from Wuhan Cell Collection Center (cell bank of China Center for Type CultureCollection).

DMEM: Gibco, USA. One bag of DMEM medium is dissolved by addition of double-distilled water; $NaHCO_3$ is added and mixed well according to the instructions; the volume is adjusted to a constant volume of 1000 mL; the PH value of the solution is adjusted with 1 mol/L HCl; after the solution is filter-sterilized or autoclaved, the solution is dispensed into 100 mL saline bottles, 90 mL solution each bottles. Before using, adjust the pH to 7.2~7.4 with 7% $NaHCO_3$, and then 10% fetal bovine serum is added.

Fetal bovine serum: Gibco, USA. The serum is placed at 4° C. in advance. When it is completely dissolved, it is then placed in a 56° C. water bath for inactivation for 30 min.

PBS: the NaCl buffer solution 8.0 g, which do not contain $Ca^{2+}$ and $Mg^{2+}$, KCl 0.2 g, $Na_2HPO_4 \cdot H_2O$ 1.56 g, and $KH_2PO_4$ 0.20 g. The solution is adjusted to 1000 mL by addition of water and the solution is then filter-sterilized.

CCK-8: purchased from Dojindo Laboratories of Japan

The trypsin: purchased from Sigma.

Investigational drug: Smilaxchinoside F, which is prepared by Guilin Sanjin Pharmaceutical Co., Ltd in accordance with Example 1 of the present invention.

Culture of the Vascular Endothelial Cell Line (ECV-304)

Human umbilical vein endothelial cells (ECV-304) are cultured in DMEM medium containing 10% fetal calf serum; then 100 units/mL of penicillin and 100 units/mL of streptomycin are added and the cells are placed in an incubator at the condition of 37° C., 5% $CO_2$ and saturated humidity. When the growth of cell fusion form into the monolayer with the culture area of up to 60% and the cell density of up to $1\times10^8$ $L^{-1}$, the culture medium is poured, the cells are washed two or three times with phosphate buffer saline and cultured in a new cell culture medium again; two or three days later, the growth of cell fusion formed into a dense monolayer, the cell density up to $1\times10^{10}$ $L^{-1}$, the culture medium is poured; the cells are digested with 0.25% trypsin and blew to simple cell; the cells are centrifuged and counted. A cell suspension of $1\times10^{5}$/mL is made for future use.

1.3 Effect of the Test Drug on ECV-304 Cell Proliferation by CCK-8 Colorimetric Method 1.3.1 Experimental Groups:

(1) normal control group (an equal amount of water is added for injection) (2) test samples group (samples are divided into eight groups with concentrations, labeled as 1-1 to 1-8). After the cells were cultured in 96-well plates for 24 hours, the drug that is 10% of the medium volume is added, respectively, according to the experimental groups. The solutions are detected at 24 h, 48 h, and 60 h respectively.

1.3.2 CCK-8 Detection of Cell Viability

The cell concentration is adjusted to $5\times10^{3}$/mL. The cells are inoculation in 96-well culture plates, 100 or 200 uL per well, and then placed in an incubator at the condition of 37° C., 5% $CO_2$ and saturated humidity for 24 h. Corresponding samples are added according to the experimental groups, 3~4 repeat wells for each group. After interaction for 24 h, 48 h, 60 h, CCK-8 solution is added to each well and the adding volume is 10% of the medium. The cells are placed in an $CO_2$ incubator at 37° C., 5% $CO_2$ for 2 hours. The absorbance (A value) of each well was measured by the microplate reader at the wavelength of 450 nm. To calculate the cells' relative survival: relative survival rate=(A value of the experimental well−A value of the control well)/A value of the control well×100%; IC50 is also calculated.

1.4 Statistical Analysis:

the results are expressed as x±s. T-test is used for saliency detection between with the data of each group.

II. Results

The results show that the compound Smilaxchinoside F has a significant inhibitory effect on EVC-304; the results are shown in Table 3, Table 4 and Table 5.

TABLE 3

The test results of the EVC-304 cells 200 uL + 10% drug, interaction for 24 h, and addition of CCK for 2 h (2-13)

| Groups | Sample final concentration mg/mL | OD value | T-test | Inhibition rate (%) |
|---|---|---|---|---|
| Blank control | — | 1.43 ± 0.16 | — | 0 |
| Sample 1-1 | 1.009 | 0.45 ± 0.03 | 1.26E−13 | 68.61 |
| -2 | 0.5045 | 0.40 ± 0.03 | 3.52E−14 | 71.87 |
| -3 | 0.25225 | 0.45 ± 0.03 | 1.34E−13 | 68.53 |
| -4 | 0.126125 | 0.49 ± 0.05 | 4.57E−13 | 65.62 |
| -5 | 0.063063 | 0.55 ± 0.05 | 2.55E−12 | 61.55 |
| -6 | 0.0315 | 0.60 ± 0.07 | 1.28E−11 | 58.06 |
| -7 | 0.01576 | 0.93 ± 0.10 | 9.14E−07 | 35.17 |
| -8 | 0.00788 | 1.09 ± 0.10 | 0.00034 | 23.48 |

According to the above data and the IC50 calculation software, this compound has an IC50 value of 0.04523167 mg/mL when work on ECV-304 for 24 hours.

TABLE 4

The test results of the EVC-304 cells 100 uL + 10% drug, interaction for 48 h, and addition of CCK for 2 h (3-19)

| Groups | Sample final concentration mg/ml | OD value | T-test | Inhibition rate (%) |
|---|---|---|---|---|
| Blank control | — | 0.35 ± 0.04 | — | 0 |
| Sapmle1-2 | 0.5045 | 0.158 ± 0.002 | 3.93E−05 | 54.42 |
| -3 | 0.25225 | 0.157 ± 0.005 | 3.72E−05 | 54.97 |
| -4 | 0.126125 | 0.167 ± 0.006 | 5.73E−05 | 51.82 |
| -5 | 0.063063 | 0.153 ± 0.006 | 4.66E−06 | 55.90 |
| -6 | 0.0315 | 0.157 ± 0.001 | 5.33E−06 | 54.71 |
| -7 | 0.01576 | 0.182 ± 0.038 | 7.68E−05 | 47.51 |
| -8 | 0.00788 | 0.182 ± 0.019 | 2.57186E−05 | 47.61 |

According to the above data and the IC50 calculation software, this compound has an IC50 value of 0.014825 mg/mL when working on ECV-304 for 24 hours.

TABLE 5

The test results of the EVC-304 cells 100 uL + 10% drug, interaction for 60 h, and addition of CCK for 2 h (3-27)

| Groups | Sample final concentration mg/ml | OD value | T-test | Inhibition rate (%) |
|---|---|---|---|---|
| Blank control | — | 2.57 ± 0.17 | — | 0 |
| Sample 1-2 | 0.5045 | 0.180 ± 0.003 | 7.53E−08 | 93.02 |
| -3 | 0.25225 | 0.176 ± 0.003 | 7.45E−08 | 93.17 |
| -4 | 0.126125 | 0.190 ± 0.015 | 7.83E−08 | 92.64 |
| -5 | 0.063063 | 0.202 ± 0.003 | 8.03E−08 | 92.16 |
| -6 | 0.0315 | 0.180 ± 0.020 | 4.29E−09 | 92.38 |
| -7 | 0.01576 | 0.219 ± 0.007 | 4.51E−09 | 91.49 |
| -8 | 0.00788 | 0.532 ± 0.064 | 1.87E−08 | 79.34 |

According to the above data and the IC50 calculation software, this compound has an IC50 value of $1.40\times10^{-6}$ mg/mL when working on ECV-304 for 24 hours.

The results show that this compound has significant inhibitory effect on ECV-304 and this inhibition shows obvious dose-effect and time-effect relationships.

3. Discussion

Angiogenesis is the process of forming new blood capillary from the formed vascular. Mainly it includes the degradation of the vascular basement membrane during activation, the activation, proliferation, migration of endothelial cells, as well as the formation of new blood vessels and vascular network during reconstruction. The formation of the blood vessel is adjusted by a large number of angiogenesis-promoting factors and inhibitory factors. Under a normal physiological state, both are in a dynamic balance. Normal new angiogenesis is involved in many physiological processes, such as embryonic development, the reconstruction of endometrium during the female menstrual cycle, etc. On the other hand, abnormal angiogenesis is a key step in many pathological processes, such as the formation of tumors, rheumatoid arthritis, diabetic retinopathy, atherosclerosis, etc. In particular, tumor formation and metastasis are dependent on the generation of new blood vessels.

Tumor growth and metastasis are dependent on angiogenesis. When the tumor is more than 1 $mm^3$-2 $mm^3$ in volume, it must rely on angiogenesis to keep growing. The neovascularization system is very important for tumor growth and metastasis, which is mainly manifested in two aspects: 1) it provides nutrition and discharges metabolite for tumor; and 2) the incompleteness of neovascular basement membrane and epithelial cells secretion of growth factors and a series of protein-degrading enzymes provide conditions for tumor cells to enter the circulation and the occurrence of possible hematogenous spread and distant metastasis. Angiogenesis is known to be a very complex pathophysiological process, and the mechanism is not yet clear. The current view holds that the main parts of the tumor angiogenesis include: 1) vascular endothelial basement membrane dissolving and endothelial cells being activated; 2) endothelial cells migrating to the tumor tissue; 3) proliferation of endothelial cells form cells cord; and 4) lumen structure and vascular adventitia being formed. In the entire process, tumor cells interact with normal endothelial cells and extracellular matrix. In addition, there still exist the participation of relevant cells and the regulation of a large number of cytokines. Wherein, cytokines include the angiogenesis induction factor and the angiogenesis inhibition factor. Under normal physiological conditions, there is a balance between them, and therefore the occurrence of neovascularization in tissue is tightly controlled; once this balance of tumor tissue is broken, it will have an obvious bias for angiogenesis. The tumor cells can produce a large number of cytokines to stimulate endothelial cell proliferation, migration, and angiogenesis. Among them, the factors with the strongest activity include acidic (aFGF) and basic fibroblast growth factor (bFGF), vascular endothelial growth factor (VEGF) and endothelial cell growth factor (EGF), etc. In a variety of tumor tissues, VEGF often exists in the region between the tumor necrosis and actively-growing cells in a large quantity, suggesting that VEGF may be an important medium in the tumor angiogenesis. A large number of VEGF receptors (VEGFR, flki/flt-1) exist on the surface of the endothelial cells while many factors control the formation of blood vessels by regulating the expression of VEGFR.

In recent years, tumor angiogenesis as a target for biological treatment has become a research focus of scientists from various countries, and they constantly develop drugs for all aspects of the tumor angiogenesis process. Currently, endostatin as an important blood vessel formation inhibitor can inhibit endothelial cell migration and tube formation, promote endothelial cell apoptosis, and inhibit the formation of new blood vessels. In China, Endostar (recombinant human vascular endothelial inhibition injection) has been combined with NP chemotherapy (vinorelbine and cisplatin, two drugs referred to as NP regimen) for the treatment of initial or retreatment III/IV non-small cell lung cancer patients, and good results have been achieved.

It was found in this experiment that this compound has a significant inhibitory activity on ECV-304, and meanwhile it has some inhibitory effect on lung cancer cells, which shows that the present compound has a good anti-tumor prospect.

Choroid, retina and corneal neovascularization lead to a variety of eye diseases and ultimate blindness; inhibiting the growth of new blood vessels is the key to the treatment of these diseases.

For arthritis patients, arthritis pannus formation and destruction of bone tissues occur in a diseased joint. The study shows the concentration of the angiogenesis stimulating factor in the intra-articular fluid was significantly increased, while the concentration of the inhibiting factor is not. Therefore it is believed that imbalance between angiogenesis stimulating factor and inhibiting factor is the key factor in the development of arthritis. Currently, inhibiting of angiogenesis has also become a hot topic of research in this field.

The above study shows that imbalance of the angiogenesis regulatory system will directly cause abnormal angiogenesis, which is a key step in many pathological processes. In recent years, the research is more closely related to diseases with excessive angiogenesis, which including diabetic retinopathy, atherosclerosis, rheumatoid arthritis, systemic sclerosis, and especially tumor formation and metastasis that are dependent on the generation of new blood vessels. Therefore, the inhibition of excessive new angiogenesis has become an important strategy for the treatment of related diseases. The compound shows significant activity in the inhibition of vascular endothelial cells, which indicates a broad application prospect in the treatment of related diseases in neovascularization.

Similar experiments are performed using Smilaxchinoside F prepared in the other examples of the present invention, and the similar results are obtained.

The invention claimed is:
1. A purified compound Smilaxchinoside F with the following structure,

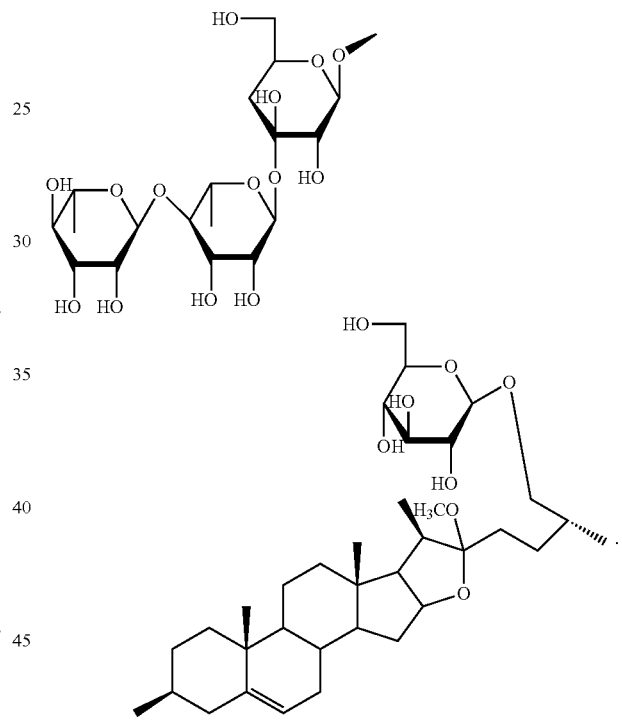

2. A separation method of Smilaxchinoside F according to claim 1, wherein said separation method comprising the following steps:
1) extraction and coarse separation
wherein the crude powder of *Smilax china* roots is extracted by organic solvents; the extraction liquid are combined; and then the organic solvents are recovered; a proper amount of water is added to form suspension liquid; the suspension liquid is extracted for 4~5 times with ethyl acetate and n-butanol sequentially; the solvents are recovered separately; and then ethyl acetate extracts and n-butanol extracts are obtained; and
2) separation of the n-butanol extracts
wherein the n-butanol extracts are adsorbed by DM130 macroporous resins, eluted with water, 25%, 50% and 75% of ethanol, respectively;
50% elution fraction of the n-butanol extracts are adsorbed by MCI gel filtration chromatography and 100~300 mesh silica gel column chromatography, eluted with 9:1:0.1~7:3:0.5 chloroform-methanol-H₂O;

a total of 31 fractions are collected; the fraction 7 to 9 are purified by Sephadex LH-20 gel filtration chromatography and are crystallized repeatedly to obtain Smilaxchinoside F compound.

3. A separation method according to claim 2, wherein said organic solvent in step 1 is 70% of acetone or ethanol or methanol.

4. A separation method according to claim 3, wherein said organic solvent in step 1 is 70% acetone.

5. A separation method according to claim 2, wherein said extraction in step 1 is impregnation extraction, reflux extraction or ultrasonic extraction.

6. A separation method according to claim 5, wherein said impregnation extraction in step 1 is, impregnation extraction at room temperature for 3-5 times; and 20~30 hours each time.

7. A separation method according to claim 5, wherein said reflux extraction in step 1 is reflux extraction for 1~3 times.

8. A separation method according to claim 5, wherein said ultrasonic extraction in step 1 is ultrasonic extraction for 1~3 times, 1~3 hours each time.

9. A separation method according to claim 6, wherein said impregnation extraction in step 1 is, impregnation extraction at room temperature for 4 times; and 24 hours each time.

\* \* \* \* \*